US008784101B1

(12) United States Patent
Engeron

(10) Patent No.: US 8,784,101 B1
(45) Date of Patent: Jul. 22, 2014

(54) RETRACTOR APPARATUS

(76) Inventor: Michael G. Engeron, Houma, LA (US)

( * ) Notice: Subject to any disclaimer, the term of this patent is extended or adjusted under 35 U.S.C. 154(b) by 1225 days.

(21) Appl. No.: 11/297,074

(22) Filed: Dec. 7, 2005

(51) Int. Cl.
*A61C 5/00* (2006.01)

(52) U.S. Cl.
USPC .......................................... 433/140; 600/242

(58) Field of Classification Search
USPC ................ 600/237–242; 433/30, 31, 93, 140; D24/152
See application file for complete search history.

(56) References Cited

U.S. PATENT DOCUMENTS

| | | | | | |
|---|---|---|---|---|---|
| D127,463 | S | * | 5/1941 | Nerbas | D24/135 |
| 2,666,428 | A | * | 1/1954 | Glenner | 600/210 |
| 2,840,070 | A | * | 6/1958 | Tofflemire | 600/246 |
| 3,651,800 | A | * | 3/1972 | Wilbanks | 600/210 |
| 4,616,633 | A | * | 10/1986 | Vargas Garcia | 600/206 |
| 4,616,634 | A | * | 10/1986 | Vargas Garcia | 600/210 |
| 5,730,597 | A | | 3/1998 | Luttrell | |
| 6,102,701 | A | | 8/2000 | Engeron | |
| 7,300,401 | B2 | * | 11/2007 | Patrickus | 600/238 |
| 2001/0034474 | A1 | * | 10/2001 | Ryan | 600/240 |
| 2004/0242970 | A1 | * | 12/2004 | Burns | 600/238 |
| 2006/0036133 | A1 | * | 2/2006 | Demsky | 600/240 |

* cited by examiner

*Primary Examiner* — Hao D Mai
(74) *Attorney, Agent, or Firm* — Garvey, Smith, Nehrbass & North, L.L.C.; Gregory C. Smith; Julia M. FitzPatrick

(57) ABSTRACT

An improved retractor device which includes a first main flat arm portion for extending along the outer surface of a patients cheek, that can be grasped by the dentist or hygienist performing the procedure; (or even in some cases, the patient); a second arm that extends into the mouth in use and is attached to the main arm at an acute angle of approximately fifty degrees and having that connecting area gently curved convexly from upper lip to lower lip and concavely from the intraoral to the extraoral portions so as to present a atraumatic surface to oral commissure, and the intraoral arm being convex as it extends to the posterior part of the mouth and getting narrower as it goes posteriorly and ending in a high convex end portion that extends behind the last tooth to reflect the cheek outwardly and posteriorly to produce an increased volume of space for conducting the dental procedure in a dry field and with greater and better comfort, access and visualization.

10 Claims, 4 Drawing Sheets

RETRACTOR APPARATUS

CROSS-REFERENCE TO RELATED APPLICATIONS

Not applicable

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The apparatus of the present invention relates to dental appliances. More particularly, the present invention relates to an improved retractor apparatus for retracting certain areas of a patient's mouth such as the lips and the cheek in order to allow greater access to the patient's mouth during dental work such as orthodontics, and particularly suited for conducting general dental, orthodontic, dental hygiene and other dental procedures in greater comfort in a dry field.

2. General Background of the Invention

Quite often in conducting dental work on a patient, such as orthodontics or the like type of operation, there is a requirement that the patient's lips and cheek be positioned so as to allow the dentist maximum access to the area of the mouth in which the operation will be conducted, which in most cases is in the area of the rear teeth such as the wisdom teeth or molars. Furthermore, during certain procedures such as those conducted by an orthodontist, it is important to retract the soft tissue away from the teeth undergoing the orthodontic procedure in order to provide comfortable access to a dry field, including the buccal surfaces of maxillary and mandibular second molars simultaneously, for allowing bonding of orthodontic appliances, such as braces, to the teeth.

While this is an important aspect of an appliance that would be utilized in order to meet these requirements, it is also important that the patient who is normally awake and aware and unanesthetized, be in as much comfort as possible during the procedure.

For example, there are appliances known in the art which have been utilized for affording access into a patient's mouth during a procedure. One of the more common types of retractors is called a Bishop retractor, which is a surgical instrument apparatus which is grasped by a standing surgeon or an assistant who holds the cheek of the patient out with one hand while he, the surgeon, conducts a surgical procedure with the other hand. The Bishop retractor is a rather simple instrument, and is used primarily, if not exclusively, in surgical procedures while the patient is anesthetized.

Secondly, U.S. Pat. No. 5,730,597, which was patented by Clifford Luttrell, and assigned to the United States of America, teaches a flat, buccal retractor which attempts to solve the problem in the art. However, this instrument's butt or end is quite narrow and sharp which would lead to discomfort for the patient, and also would not allow for keeping soft tissue and saliva out of the field in an orthodontic procedure. The narrow sharp-ended cheek retractor of Luttrell is designed to be used in an operating room setting by a standing surgeon on a fully anesthetized patient. It is designed to retract unsurgerized tissue to allow access to soft tissue on the stretch to facilitate surgerizing the stretched tissue. Furthermore, it could be used to retract surgerized tissue to allow visualization of, and access to, the bony maxilla or mandible beneath the soft tissue in order to allow instrumentation, irrigation, and cutting of the bony jaw with a rotary or reciprocating instrument. Again, these procedures are normally done in a wet field on an anesthetized patient by a standing surgeon.

The Luttrell instrument, in one embodiment, retracts either the left upper lip or the right lower lip, but not simultaneously. The other, mirror form of the instrument retracts the left lower lip or right upper lip, but again, not simultaneously. Therefore, there is a need in the industry for providing an improved universal retractor apparatus that is applicable for retracting the cheek, lips and commissure to expose the left upper and lower posterior teeth and, when used for the other side of the mouth to expose the right upper and lower posterior teeth. That is to say, one instrument, to be used in a universal manner, to provide retraction in all four quadrants of the mouth to comfortably expose, with excellent access and viability, all the posterior teeth comfortably in a dry field. The instrument, in this new embodiment, is shaped in such a way as to provide retraction in four quadrants to provide universal access to and excellent visualization of all posterior teeth in a dry field and in comfort for the unanesthetized patient. Furthermore, there is a need to allow such a device to be utilized wherein the dentist or orthodontist may conduct the procedure while being seated rather than having to hover over the patient, which one may have to do if one utilized the Luttrell device in the procedure.

In addition, the present inventor has obtained U.S. Pat. No. 6,102,701, which provides for an instrument that is provided in a set of two specific instruments, one for the right side providing access and visualization of right upper and lower teeth and a different, mirror image, instrument used similarly on the left side. The present instrument is an improvement in that it is universal, providing access, visualization and a dry field on both the right and left sides and is provided as a single instrument for universal use. Also, the biconvex end portion that extends behind the last molar and is positioned at the end of the intraoral arm is shaped in such a way to provide better access to the back of the last tooth as it traverses the anterior edge of the ascending ramus of the mandible and is therefore much more comfortable in use than the instrument provided in U.S. Pat. No. 6,102,701.

Also, U.S. Pat. No. 6,102,701 provides for the extraneous parts specifically used for depressing the lower lip and elevating the upper lip. The part of the present instrument that retracts the lip commissure also depresses the lower lip and elevates the upper lip, thereby precluding the need for instrument parts devoted specifically to lower lip depression or upper lip elevation.

The present instrument is an improvement over U.S. Pat. No. 6,102,701 in that it, in one universal instrument instead of two instruments in a set, simplifies manufacturing and maintenance by eliminating extraneous parts and improves the functioning of the present embodiment by allowing better and more comfortable access to and visualization of the posterior of the last tooth by improving the way the intraoral posterior biconvex part traverses the anterior part of the ascending ramus of the mandible.

BRIEF SUMMARY OF THE INVENTION

The improved retractor device includes a first main flat arm portion for extending along the outer surface of a patients cheek, that can be grasped by the dentist or hygienist performing the procedure; (or even in some cases, the patient); a second arm that extends into the mouth in use and is attached to the main arm at an acute angle of approximately fifty degrees and having that connecting area gently curved convexly from upper lip to lower lip and concavely from the intraoral to the extraoral portions so as to present an atraumatic surface to the oral commissure; the intraoral arm being convex as it extends to the posterior part of the mouth and narrowing as it extends posteriorly and terminates in a biconvex end portion that extends behind the last tooth to retract the cheek outwardly and posteriorly to produce an increased volume of space for conducting the dental procedure in a dry field and with greater comfort and better access and visualization.

The main arm of the retractor extends along the outer surface of the cheek during use and ends in a curved end that bends 180 degrees back on itself providing a curved surface that can be used to hook the finger in for manipulating the instrument by the dentist or patient. The sides of the main arm of the retractor diverge five degrees as you approach the curved end of the arm to insure that the hand does not slip on the handle during use.

Therefore, it is a principal object of the present invention to provide an improved universal retractor apparatus for retracting certain areas of a patient's mouth, for conducting general dental, orthodontic, dental hygiene and other dental procedures in a dry field, so that the single instrument can be utilized on both sides of the patient's mouth for upper and lower teeth simultaneously.

It is a further principal object of the present invention to provide an improved retractor that can be used by the person performing orthodontic work which includes a biconvex end portion of the second end for resting to the rear of the last tooth, the biconvex end portion traversing the anterior part of the ascending ramus of the mandible to produce an increased volume of space for conducting the dental procedure in a dry field with greater access, comfort and visualization.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein like reference numerals denote like elements and wherein.

DETAILED DESCRIPTION OF THE INVENTION

Figure 1:
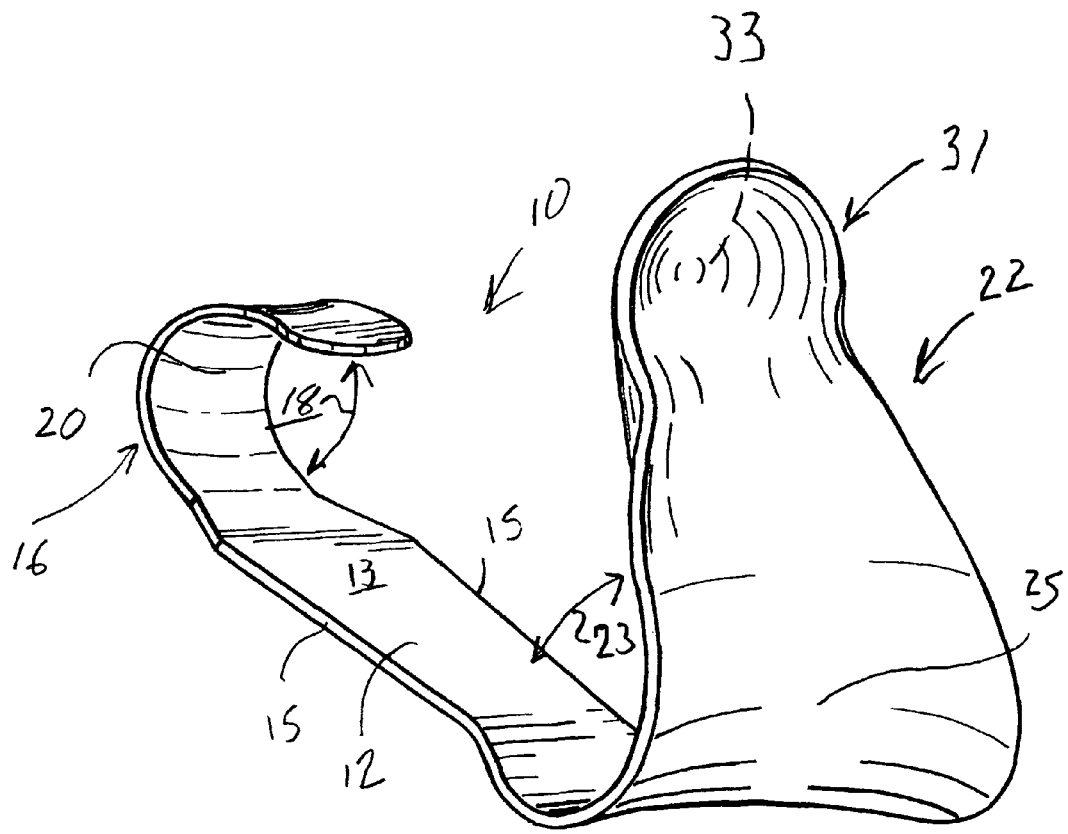
FIG. 1 is a perspective view of the preferred embodiment of the apparatus of the present invention.
Figure 2:
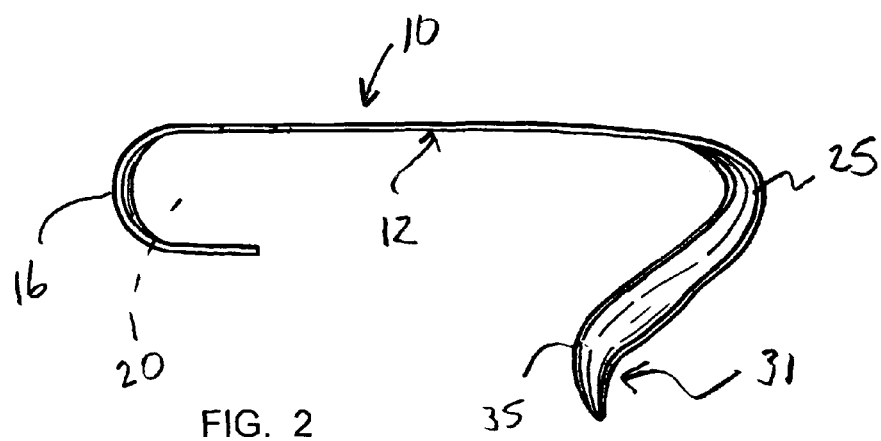
FIG. 2 is a side view of the preferred embodiment of the apparatus of the present invention.
Figure 3:
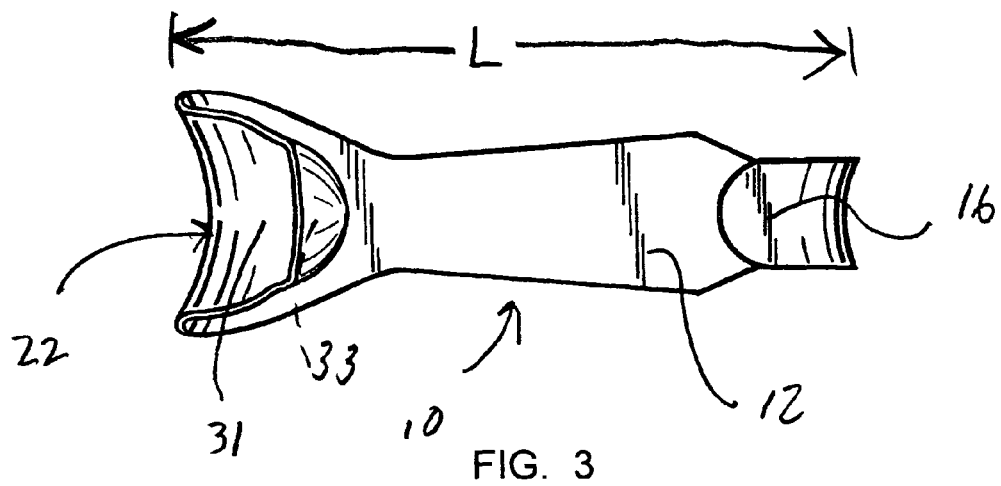
FIG. 3 is a top view of the preferred embodiment of the apparatus of the present invention.
Figure 4:
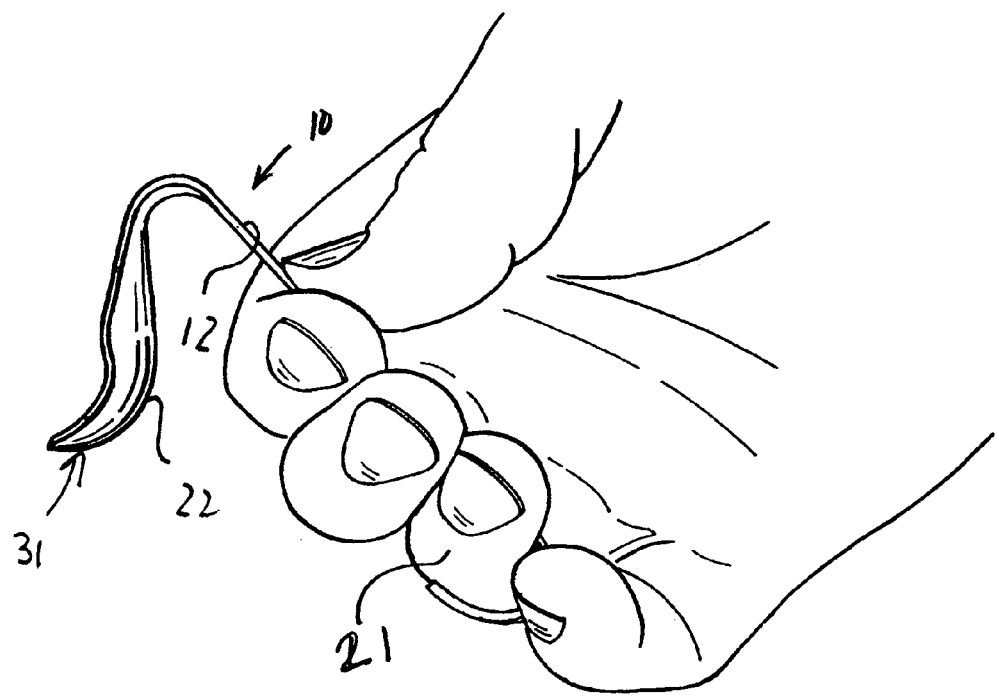
FIG. 4 is a view of the preferred embodiment of the apparatus of the present invention in a person's grasp.
Figure 5:
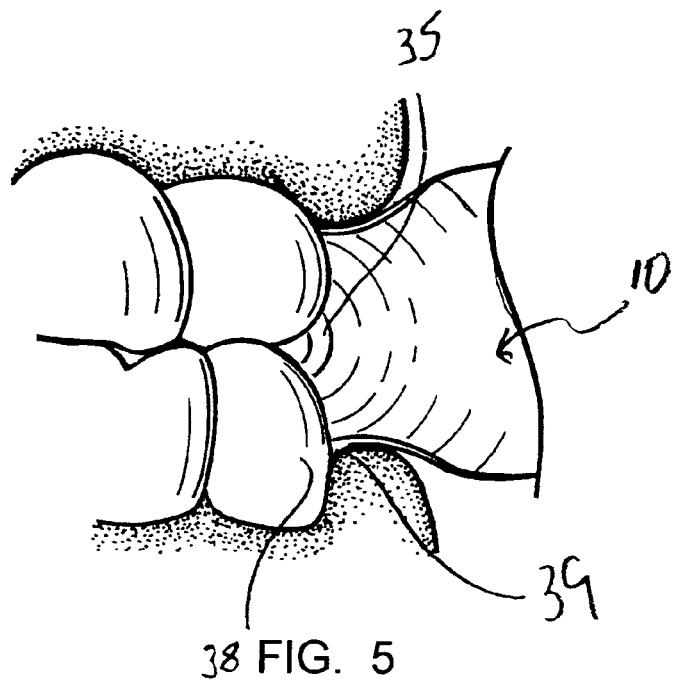
FIG. 5 is a partial view of the preferred embodiment of the apparatus positioned behind the tooth and against the ascending ramus of the jaw.
Figure 6:
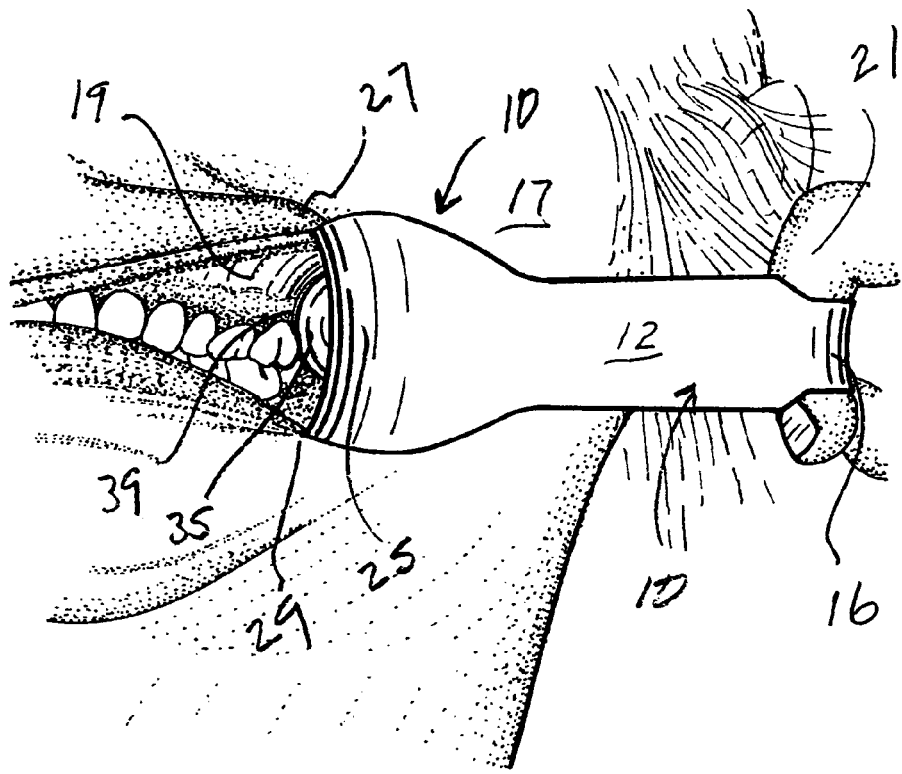
FIG. 6 is an overall view of the apparatus as seen in position in partial view in FIG. 5.

FIGS. 1 through 3 illustrate perspective, side and top views respectively of the improved retractor device 10 of the present invention, while FIGS. 4 through 6 illustrate views of the present invention being used with a patient. As illustrated, device 10 comprises a first main arm portion 12, having a flat surface 13, with divergent sides 15 along its length. As will be seen in further views, the flat surface 13 will extend along the outer surface of a patient's cheek 17, as seen in FIG. 6, when the instrument is put into use. As illustrated in FIG. 6, the main arm terminates first in a curved end 16 which defines a 180 degree bend 18, to define an opening 20, through which the dentist, hygienist, or even the patient can grasp with his or her finger 21, as the retractor retracts the cheek when in use. There is provided on the second end of the arm 12 a retractor portion 22, which is attached to the main arm 12 at approximately a 50 degree convexly curved angle 23. The arm includes a connecting area 25 gently curved convexly from the upper lip 27 to the lower lip 29, as seen in FIG. 6. The area 25, at end 31, then defines a concave curved area 33, which extends from the intraoral to the extraoral portions, so as to present an atraumatic surface 35 to the oral commissure 39, as seen in FIGS. 5 and 6.

As illustrated in FIGS. 4 through 6, the intraoral arm portion 32 is biconvex in shape, so that as it narrows down in width, and is positioned into the posterior portion of the patient's mouth, it would be positioned in a high convex end portion that would extend behind the last tooth 38, while the intraoral posterior biconvex portion 32 traverses the anterior part of the ascending ramus of the mandible.

As seen in FIGS. 5 and 6, apparatus 10 is engaging the commissure 39 of the patient's mouth on the right side to facilitate lateral and posterior retraction of the commissure 39 to provide enhanced access to the buccal surfaces of bicuspid and molar teeth 38 for orthodontic bonding, while cheek 17 is reflected outwardly and posteriorly to produce an increased volume of space for conducting the dental procedure in a dry field and with greater and better access and visualization. During this procedure, as seen in FIG. 6, the flat arm 12 is resting against the cheek 17 of the patient, and the curved, distal end 16, defining the space 20, is being grasped by the finger 21 of the dentist, or hygienist, or in some cases, the patient himself.

In FIG. 4, the device 10 is seen being grasped in the hand 37 of the dentist, so that the loop 20 is held by the third (ring) finger 21, and the retractor portion 22 extends from the hand to be inserted in the patient's mouth.

What is very important in the design of this device 10, is that the device 10 can be used in a universal manner on both the left and right sides of the mouth 19 of a patient, without having to utilize a separate device for each side, as with the prior art retractor. As seen in FIG. 3, the device is symmetrical in its design along its length L, so that it can be moved between left and right cheeks very efficiently.

Figure 7:
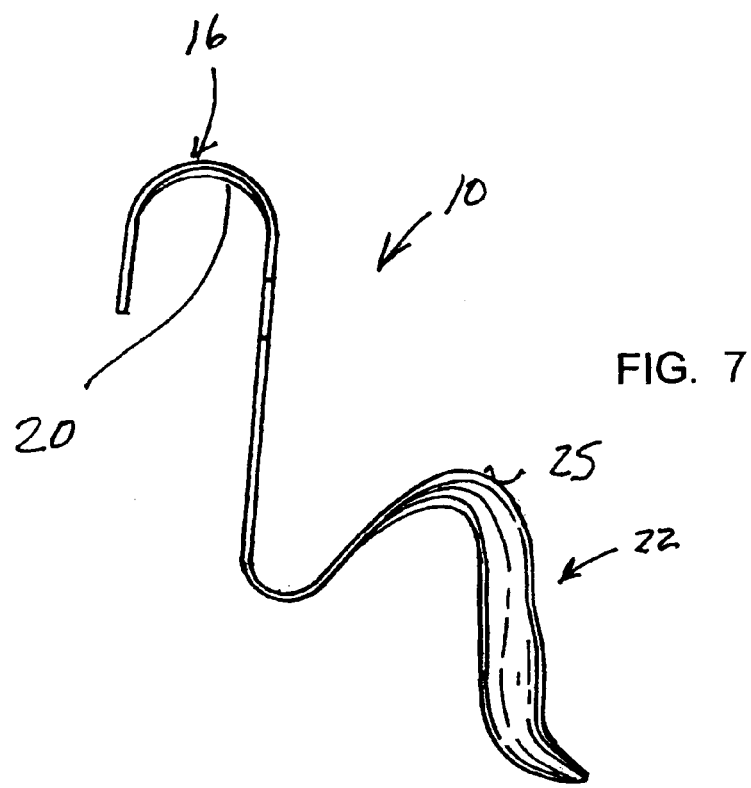
FIG. 7 is a side view of an alternate embodiment of the present invention.
Figure 8:
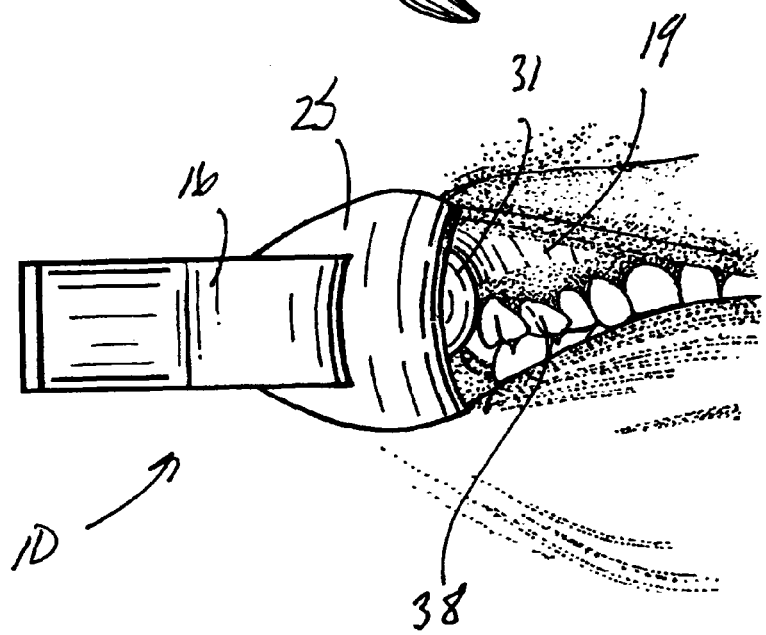
FIG. 8 is the embodiment illustrated in FIG. 7 in position in a patient's mouth.

FIGS. 7 and 8 illustrate an alternate embodiment of the present invention 10, so that rather than the retrator portion 22 and the grasping end 16 are turned inward toward one another, as seen in FIG. 2, in the design as seen in FIGS. 7 and 8, the main arm 12 has the grasping end 16 extending in a first direction forming the opening 20, to grasp with one's finger, while the retracting portion 22 is formed away from the main arm 12 in the opposite direction and, when in use, the convex surface 25 pulls the lips 27, 29 open, with the end 31 positioned behind the last tooth 38 of the patient, as seen in FIG. 8.

The following is a list of parts and materials suitable for use in the present invention.

PARTS LIST

| Part Number | Description |
| --- | --- |
| 10 | device |
| 12 | main arm portion |
| 13 | flat surface |
| 15 | parallel sides |
| 17 | cheek |
| 18 | 180° bend |
| 19 | mouth |
| 20 | opening |
| 21 | finger |
| 22 | retractor portion |
| 23 | convexly curved angle |
| 25 | connecting area |
| 27 | upper lip |
| 29 | lower lip |
| 31 | end |
| 32 | intraoral arm portion |
| 33 | concave curved area |
| 37 | hand |
| 38 | tooth |
| 39 | commissure |

All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

The invention claimed is:

1. An improved retractor apparatus, positionable within either a left or right cheek of a patient, comprising:
   a. a main arm portion;
   b. a first end of the main arm portion graspable by a person administering dental care;
   c. a second end of the main arm portion extending at an acute angle approximating 45 degrees from the main arm portion defining a space therebetween, the second end also including an enlarged area having superior and inferior projections symmetrically off from the main arm portion for defining a means to engage a commissure of the patient's mouth on either the right or left side within the space to facilitate lateral and posterior retraction of the commissure and cheek to provide enhanced access to buccal surfaces of bicuspid and molar teeth for orthodontic bonding;
   d. a biconvex end portion of the second end for resting to a rear of a most posterior tooth, to produce an increased volume of space for conducting a dental procedure in a dry field with greater access, comfort and visualization.

2. The device in claim 1, wherein the first end comprises an open loop for grasping by the person administering the dental care.

3. The device in claim 1, wherein the main arm portion rests along the outer surface of the cheek when the device is placed within the mouth of the patient, said main arm having divergent sides that prevent the fingers from slipping off the main arm portion while in use.

4. The device in claim 1, wherein, when in use, the biconvex end portion traverses the anterior part of the ascending ramus of the mandible to produce an increased volume of space for conducting the dental procedure in greater comfort in the dry field.

5. The device in claim 1, wherein the angle at which the second end is to the main arm is between 40-50 degrees.

6. An improved retractor apparatus, positionable within either left or right cheeks of a patient, comprising:
   a. a flat main arm portion;
   b. a first end of the flat main arm portion which defines an open loop graspable by a person administering dental care;
   c. a second end of the main arm portion extending at an acute angle from the main arm portion to define a space therebetween, the second end also including an enlarged convex area having superior and inferior projections symmetrically off from the main arm portion for defining a means to engage a commissure of the patient's mouth on either the right or left side within the defined space to facilitate posterior and lateral retraction of the commissure and cheek to provide enhanced access to the buccal surfaces of the bicuspid and molar teeth for orthodontic bonding;
   d. a biconvex end portion of the second end for resting to a rear of a most posterior tooth, to produce an increased volume of space for conducting a dental procedure in a dry field with greater comfort, access and visualization.

7. The apparatus in claim 6, wherein the acute angle between the main arm and the second end is approximately 50 degrees.

8. The apparatus in claim 6, wherein the first end defining the open loop and the acute angle formed at the second end of the main arm are curved inwardly along the same surface of the main arm.

9. The apparatus in claim 6, wherein the first end defining the open loop and the acute angle formed at the second end of the main arm are curved inwardly along the same surface of the main arm.

10. An improved retractor apparatus, positionable within either left or right cheek of a patient, comprising:
   a. a flat main arm portion positionable along the outer surface of the cheek;
   b. a first end of the flat main arm portion which defines an open loop graspable by a person administering dental care;
   c. a second end of the main arm portion extending at an acute angle from the main arm portion and defining a space therebetween, including an enlarged convex area having superior and inferior projections symmetrically off from the main arm portion for defining a means to engage a commissure of the patient's mouth on either the right or left side within the defined space to facilitate posterior and lateral retraction of the commissure during a process of orthodontic bonding;
   d. a biconvex end portion of the second end for resting to a rear of a most posterior tooth, the biconvex end portion traversing an anterior part of an ascending ramus of a mandible to produce an increased volume of space for conducting the dental procedure in a dry field with greater comfort, access and visualization, and a part of the second end that intervenes between the part that retracts the commissure and a biconvex part that traverses the ascending ramus of the mandible retracts the cheek laterally and posteriorly to enhance the access and visualization for conducting the dental procedure.

* * * * *